United States Patent [19]

Tipton et al.

[11] Patent Number: 5,632,727

[45] Date of Patent: *May 27, 1997

[54] BIODEGRADABLE FILM DRESSING AND METHOD FOR ITS FORMATION

[75] Inventors: Arthur J. Tipton, Birmingham, Ala.; Shawn M. Fujita, Amsterdam, Netherlands; Richard L. Dunn, Fort Collins, Colo.

[73] Assignee: Atrix Laboratories, Inc., Ft. Collins, Colo.

[*] Notice: The term of this patent shall not extend beyond the expiration date of Pat. No. 5,324,519.

[21] Appl. No.: 487,547

[22] Filed: Jun. 7, 1995

Related U.S. Application Data

[62] Division of Ser. No. 336,017, Nov. 8, 1994, which is a continuation of Ser. No. 70,499, Jun. 2, 1993, abandoned, which is a continuation of Ser. No. 849,896, Mar. 12, 1992, abandoned, which is a continuation-in-part of Ser. No. 788,032, Dec. 23, 1991, Pat. No. 5,340,849, which is a division of Ser. No. 513,782, Apr. 24, 1990, Pat. No. 5,278,201, which is a division of Ser. No. 252,645, Oct. 3, 1988, Pat. No. 4,938,763.

[51] Int. Cl.$^6$ ................................................. A61F 13/00
[52] U.S. Cl. ......................... 602/47; 602/904; 602/900; 424/426; 604/890.1
[58] Field of Search ........................ 604/890.1, 891.1, 604/892.1, 19; 424/78.09, 424, 426, 443–449; 602/43, 46, 47, 900, 904

[56] References Cited

U.S. PATENT DOCUMENTS

| | | |
|---|---|---|
| 2,155,658 | 4/1939 | Herrmann . |
| 2,624,690 | 1/1953 | Leader et al. ............... 602/904 |
| 3,379,554 | 4/1968 | Brindamour . |
| 3,577,516 | 5/1971 | Gould . |
| 3,832,459 | 8/1974 | Berkeley . |
| 3,836,647 | 9/1974 | Lange . |
| 3,847,155 | 11/1974 | Bernaola . |
| 3,878,138 | 4/1975 | Keegan et al. . |
| 3,880,158 | 4/1975 | Gurney . |
| 3,887,699 | 6/1975 | Yolles . |
| 3,912,665 | 10/1975 | Spitzer et al. . |
| 3,912,667 | 10/1975 | Spitzer et al. . |
| 3,932,602 | 1/1976 | Sweger . |
| 3,935,308 | 1/1976 | Wise . |

(List continued on next page.)

FOREIGN PATENT DOCUMENTS

| | | |
|---|---|---|
| 0159293 | 10/1985 | European Pat. Off. . |
| 407903 | 1/1991 | European Pat. Off. ............... 602/46 |

(List continued on next page.)

OTHER PUBLICATIONS

Encyclopedia of Polymer Science and Engineering, vol. 2, pp. 236–237 (Biodegradable Polymers), John Wiley & Sons, Inc. (1985).

Billmeyer, Textbook of Polymer Science (Third Edition), pp. 390–391, John Wiley & Son, New York.

(List continued on next page.)

*Primary Examiner*—Corrine M. McDermott
*Assistant Examiner*—Chalin Smith
*Attorney, Agent, or Firm*—Merchant & Gould, Smith, Edell, Welter & Schmidt

[57] ABSTRACT

The invention is directed to a biodegradable film dressing with or without additional therapeutic agents, an apparatus for spray delivery and a method for formation of the film dressing on a human or animal tissue. The film dressing is formed from a liquid composition of at least one biodegradable/bioerodible thermoplastic polymer in a pharmaceutically acceptable solvent. The spray apparatus includes a vessel containing the liquid composition with a dispensing means. The film is formed by dispensing, preferably by spraying, the liquid composition onto a tissue site and contacting the liquid composition with an aqueous based fluid to coagulate or solidify the film onto the human or animal tissue. The biodegradable film can be used to protect and to promote healing of injured tissue and/or to deliver biologically active agents.

22 Claims, 2 Drawing Sheets

U.S. PATENT DOCUMENTS

| | | | |
|---|---|---|---|
| 3,936,402 | 2/1976 | Keegan et al. | |
| 4,001,151 | 1/1977 | Keegan et al. | |
| 4,122,158 | 10/1978 | Schmitt | |
| 4,156,067 | 5/1979 | Gould | 528/73 |
| 4,186,190 | 1/1980 | Gregory | |
| 4,382,919 | 5/1983 | Alonso et al. | |
| 4,495,169 | 1/1985 | Schmolka | |
| 4,508,705 | 4/1985 | Chaudhuri et al. | |
| 4,534,958 | 8/1985 | Adams et al. | |
| 4,534,959 | 8/1985 | Schmolka | |
| 4,542,012 | 9/1985 | Dell | |
| 4,579,731 | 4/1986 | Fox, Jr. et al. | |
| 4,585,647 | 4/1986 | Schmolka | |
| 4,588,581 | 5/1986 | Schmolka | |
| 4,614,787 | 9/1986 | Szycher et al. | |
| 4,631,188 | 12/1986 | Stoy | |
| 4,683,142 | 7/1987 | Zimmermann et al. | 427/2 |
| 4,743,440 | 5/1988 | Callingham et al. | |
| 4,780,320 | 10/1988 | Baker | |
| 4,783,340 | 11/1988 | McDonell et al. | |
| 4,791,149 | 12/1988 | Pocknell | |
| 4,822,596 | 4/1989 | Callingham et al. | |
| 4,899,762 | 2/1990 | Muller | |
| 4,921,691 | 5/1990 | Stockel | |
| 4,931,282 | 6/1990 | Asmus et al. | |
| 4,933,182 | 6/1990 | Higashi et al. | |
| 4,938,763 | 7/1990 | Dunn et al. | |
| 4,946,870 | 8/1990 | Partain, III et al. | |
| 4,981,696 | 1/1991 | Loomis | |
| 4,997,425 | 3/1991 | Shioya | |
| 5,013,553 | 5/1991 | Southard | |
| 5,077,049 | 12/1991 | Dunn | |
| 5,192,536 | 3/1993 | Huprich | 424/78.08 |
| 5,274,074 | 12/1993 | Tang et al. | 528/370 |
| 5,278,201 | 1/1994 | Dunn et al. | |
| 5,278,202 | 1/1994 | Dunn et al. | |
| 5,324,519 | 6/1994 | Dunn | |
| 5,324,520 | 6/1994 | Dunn et al. | |
| 5,340,849 | 8/1994 | Dunn et al. | |
| 5,368,859 | 11/1994 | Dunn et al. | |
| B1 4,938,763 | 7/1995 | Dunn et al. | |

FOREIGN PATENT DOCUMENTS

| | | | |
|---|---|---|---|
| 0521455A2 | 1/1993 | European Pat. Off. | |
| 0537559 | 4/1993 | European Pat. Off. | |
| 0560014 | 9/1993 | European Pat. Off. | |
| 0649662 | 4/1995 | European Pat. Off. | |
| 2126270 | 10/1972 | France | |
| 2924042 | 2/1980 | Germany | 602/904 |
| 120602 | 8/1958 | New Zealand | |
| 160347 | 6/1972 | New Zealand | |
| 801170 | 9/1958 | United Kingdom | 602/904 |
| WO 90/00066 | 1/1990 | WIPO | |

OTHER PUBLICATIONS

Gilding, Biodegradable Polymers (Chapter 9), pp. 210–232, Biocompatibility of Clinical Implant Materials.

Hawley's Condensed Chemical Dictionary (llth Ed.) pp. 224, 555 and 567, Van Nostrand Reinhold Co., NY, NY.

Holland, Polymers for Biodegradable Medical Devices, 1. The Potential of Polyesters and Controlled Macromolecular Release Systems, J. of Controlled Release 4: 155–180 (1986).

U.S. Application S/N 528,056 (select pages) Stoy.

BIODEGRADABLE FILM DRESSING AND METHOD FOR ITS FORMATION

CROSS-REFERENCE TO RELATED APPLICATIONS

This application is a divisional of U.S. patent application Ser. No. 08/336,017, filed Nov. 8, 1994, which is a continuation of U.S. patent application Ser. No. 08/070,499, filed Jun. 2, 1993, now abandoned, which is a continuation of U.S. patent application Ser. No. 07/849,896, filed Mar. 12, 1992, now abandoned, which is a continuation-in-part of U.S. patent application Ser. No. 07/788,032, filed Dec. 23, 1991, now U.S. Pat. No. 5,340,849 (issued Aug. 23, 1994), which is a division of U.S. patent application Ser. No. 07/513,782, filed Apr. 24, 1990, now U.S. Pat. No. 5,278,201 (issued Jan. 11, 1994), which is a division of U.S. patent application Ser. No. 07/252,645, filed Oct. 3, 1988, now U.S. Pat. No. B1-4,938,763 (issued Jul. 3, 1990), which applications are incorporated by reference.

BACKGROUND

Coverings or dressings applied to the surface of human or animal tissues can be used to protect tissue injuries, to deliver pharmaceutical or therapeutical agents and to promote wound healing. In the case of conventional therapy for most surgical and trauma wounds, including burns, one stage of treatment requires a semi-permanent covering or dressing. The purposes of this dressing can include mechanical protection of the wound, prevention of microbial contamination, prevention of wound dehydration, removal of wound exudate, and delivery of high local levels of a therapeutic agent. As wound treatments vary depending on the type and severity of the wound, several natural and/or synthetic dressings have been developed for short and long-term application. However, most of these dressings have one or more disadvantages including the need for frequent removal, difficulty in adhesion, improper mechanical properties, or difficulty in application.

Most currently available topical therapeutic formulations used with dressings are inefficient. This inefficiency results because of loss of the therapeutic agents through perspiration and mechanical action, inability of the agent to penetrate skin and mucous membranes, and crystallization or precipitation of the agents at the tissue site. Some topical therapeutic formulations are incorporated into the materials forming the dressings to be applied as patches, preformed sheets or by spray. More typically, wound coverings or dressings are used with ointments of a topical antibiotic and/or antifungal formulations. Whether used with or without dressings, topical formulations in the form of creams, ointments or liquids are difficult to apply and maintain at the injury site. They are rapidly removed by mechanical action and/or body fluid dissolution. If used in combination with a dressing, therapeutic formulations have several other drawbacks including lack of biodegradability, damage or irritation to the skin during removal of the dressing, covalent bonding or other interaction of the therapeutic agent and the dressing, inability to use a wide variety of therapeutic agents, and inadequate adhesion of the dressing.

Therefore, it is an object of the present invention to provide for a film covering or dressing for biological tissue. Another object is to provide for spray delivery of a liquid composition containing a biodegradable or bioerodible polymer which will convert to the film covering. Another object is to provide an apparatus for the spray delivery. Another object is to provide for the formation of a film dressing which is biodegradable and does not require removal from the surface of tissue while still maintaining good adhesive qualities. Another object is to provide for the formation of a film which is a semi-permeable barrier to oxygen and water while providing mechanical protection to the surface of the tissue including a barrier to organisms associated with infection. A further object is to provide for formation of a film which is capable of delivery of at least one biologically-active agent over a desired period of time. Yet another object is to provide a method for promoting wound healing on a wide variety of injured tissues like skin, mucous membranes, bones and nerves.

SUMMARY OF THE INVENTION

These and other goals are achieved by the present invention, which is directed to a biodegradable film with or without additional therapeutic agents, an apparatus for spray delivery of the biodegradable film, and a method for formation of the film on an animal tissue. The biodegradable film can be used to provide protection and promote healing of injured tissue and/or for delivery of biologically active agents or substances.

The biodegradable film dressing or covering of the present invention provides an adhesive, strong, flexible, biodegradable, mechanical and microbial barrier and/or pharmaceutical delivery system for protection and/or treatment of tissue. The film is formed from a liquid composition of at least one biodegradable or bioerodible, substantially water-insoluble, non-reactive thermoplastic polymer in a pharmaceutically acceptable solvent which may optionally contain a biologically active agent. The thermoplastic polymer preferably has a molecular weight and a concentration in the liquid composition to achieve a viscosity that allows the composition to be aerosolized and also to provide a film which is adhesive, cohesively strong and a mechanical and microbial barrier. The thermoplastic polymer also preferably has a low glass transition temperature (Tg) to provide for a soft and flexible film. The thermoplastic polymer can also be sufficiently hydrophilic to provide for diffusivity of water, oxygen, and nutrients through the film. The film can be microporous if a pore forming agent is added, or can be substantially nonporous. The film can also have low oxygen and water permeability. Other desired film properties can be achieved by adding one or more of the following components to the liquid composition: plasticizers, colorants, biologically active agents, and/or agents which enhance release or percutaneous absorption of the biologically active agents.

To form the film dressing, the liquid composition is dispensed to the tissue site, whereupon the solvent diffuses or dissipates into the surrounding tissues or into an aqueous layer applied after the film dressing. Upon contact with an aqueous based fluid, the thermoplastic polymer, which is substantially insoluble in the aqueous based fluid, coagulates or solidifies to form a microporous film or gelatinous matrix. The liquid composition can also be comprised of a thermoplastic polymer in a liquid aerosol propellant. The composition is sprayed onto a tissue site, and, as the aerosol propellant evaporates, the thermoplastic polymer coagulates to form a film or gelatinous matrix.

In a preferred version, the film dressing is microporous and has a two-layered pore structure composed of a core portion and a skin portion. The skin portion has pores with diameters significantly smaller than those of the core portion. The pores are formed as the solvent or pore forming agent diffuses out of the coagulating or solidifying film and into the surrounding tissue or aqueous fluids. The skin portion can be formed on top of the core portion with the core portion or layer in contact with the tissue, or the skin portion layer can be under the core portion and in contact with the tissue. Alternatively, the film dressing can have a homogeneous microporous structure, with pores evenly distributed throughout the film.

Several factors influence the size and distribution of the pores formed in the film dressing. For example, the addition of a pore forming agent to the liquid composition will produce a film having about the same diameter pores throughout the film. The size and/or quantity of the pore forming agent as well as the distribution of the agent in the coagulating or solidifying film can influence pore size and number in the film. It is preferred that the size and number of pores of the film dressing facilitate diffusion of nutrients, oxygen, water and the biologically active agents. It is further preferred that the degree of porosity in the matrix provides for a film which is capable of substantially maintaining structural integrity for the desired period of time without cracking or breaking up during use.

The liquid composition can further contain at least one biologically active agent which provides a biological, physiological or therapeutic effect in a human or animal. The biologically active agent is incorporated in the film dressing and is subsequently released into the surrounding tissue. The biological agent can act to enhance cell growth and tissue regeneration, cause nerve stimulation or bone growth, prevent infections, promote wound healing and/or provide pain relief. Accordingly, the invention provides for a film dressing capable of functioning as a delivery system of drugs, medicaments, and other biologically active agents to tissues. Preferably, the film can act as a sustained or timed release matrix.

Additives can also be incorporated into the liquid composition to effect both drug release and mechanical properties. Plasticizers increase the flexibility of the microporous film dressing. Agents can be added to modify the release of drugs and/or to enhance percutaneous absorption of the drug after release.

The spray apparatus of the invention includes a vessel with a dispensing means for spray delivery of the liquid composition located within the vessel. The type of vessel employed depends on the choice of dispensing means and includes cans or bottles of glass, plastic or metal. The dispensing means can be a pump, a fluid pressurizing component, a collapsible vessel with a tube or jet, or an aerosol propellant with associated valve mechanisms. Generally, any chemical, mechanical or electronic mechanism for propelling the liquid composition as a liquid stream, liquid droplets or atomized spray from the vessel is appropriate as the dispensing means. The preferred dispensing means is a compatible liquid or gaseous aerosol propellant with a valve mechanism which enables atomized spray delivery of the liquid composition onto a human or animal tissue.

The method of forming the biodegradable film dressing on a human or animal tissue involves dispensing the liquid composition of biodegradable or bioerodible thermoplastic polymer with an optional bioactive agent in an organic solvent onto the human or animal tissue and contacting the liquid composition with an aqueous-based fluid to coagulate or solidify the film onto the human or animal tissue. As the organic solvent dissipates or diffuses into the surrounding tissue or aqueous-based fluid, the thermoplastic polymer comes into contact with the aqueous-based fluid, and since the thermoplastic polymer is substantially insoluble in the aqueous-based fluid, it coagulates or solidifies to form a film dressing. The aqueous-based fluid can be a body fluid present on the surface of the tissue or an aqueous-based fluid applied to the tissue before or after application of the liquid composition. The liquid composition and/or aqueous-based fluid can be administered to the tissue site by any suitable method for applying a liquid, as for example, by squirting, painting, brushing, and preferably by spraying the composition onto the tissue site.

The invention also provides a method of using the film dressing to treat injured tissue of a human or animal and to administer biologically active agents by topical transport through the skin of a human or animal. The method involves administering to a human or animal one of the foregoing compositions in an amount effective to form a film dressing. The film dressing optionally contains at least one biologically active agent, which acts to enhance cell growth and/or tissue formation, or to prevent the growth of infectious agents, or to reduce pain and/or inflammation or, in the alternative, if drug delivery is contemplated, can act according to its recognized biological activity. The film dressing can also serve to bind tissue together, like a suture or hold tissue apart, like a surgical barrier. The liquid composition is administered to skin, a surgical incision, a burn, a body cavity, or to a site of tissue injury. The film dressing of the present invention provides a cohesively strong, adhesive, biodegradable, mechanical and microbial barrier capable of protecting and promoting healing of the injury.

DETAILED DESCRIPTION OF THE INVENTION

Figure 1:
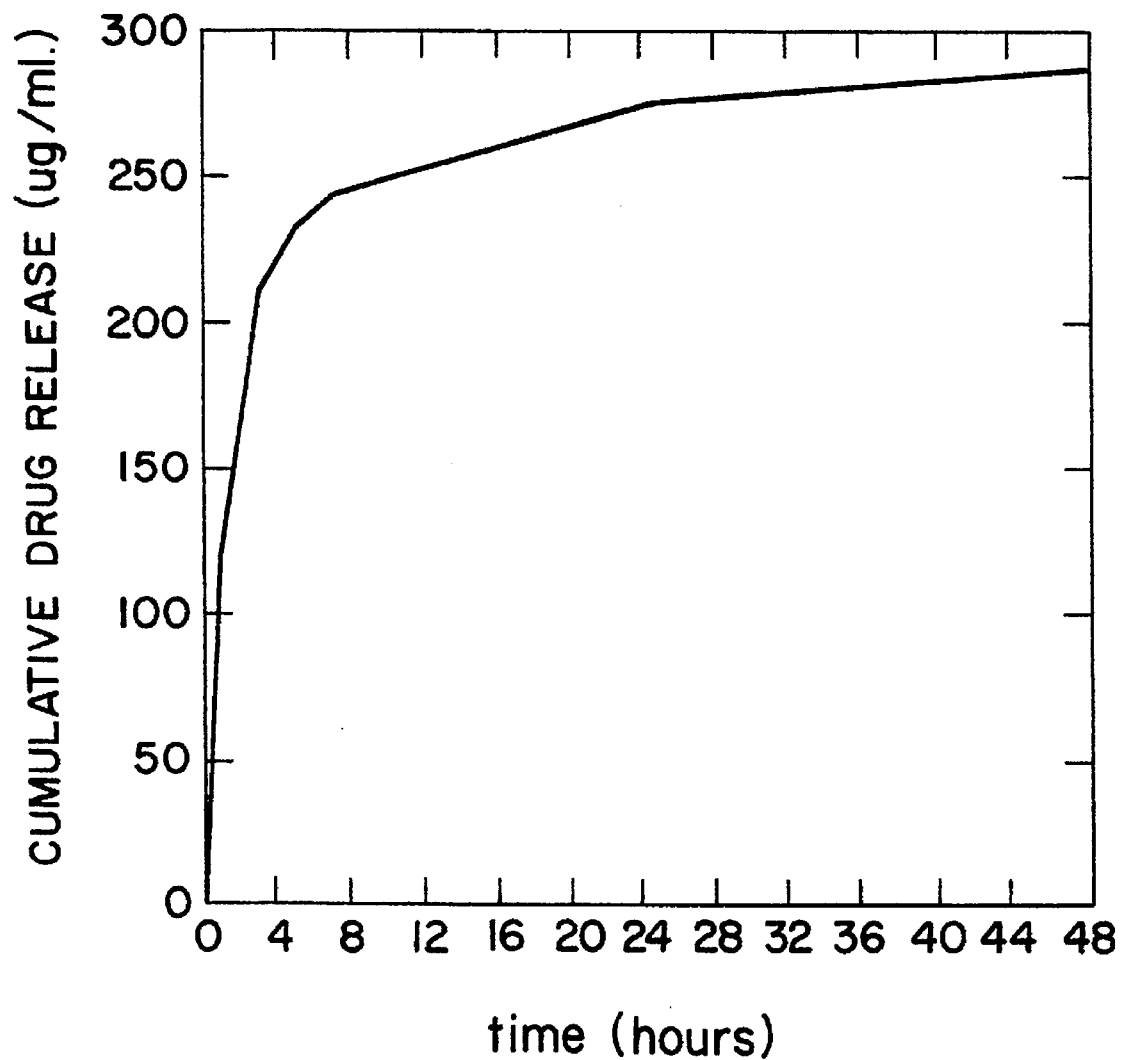
FIG. 1 summarizes the cumulative release of doxycycline from the polymer film over time.

The biodegradable film dressing or covering is formed from a liquid composition of at least one biodegradable or bioerodible, substantially water-insoluble, non-reactive thermoplastic polymer in a pharmaceutically acceptable organic solvent. Alternatively, the liquid composition is composed of a biodegradable thermoplastic polymer in a liquid aerosol propellant. Optionally, the liquid composition can include a pore forming agent, plasticizers, colorants, biologically active agents, and/or agents which enhance release or percutaneous absorption of the biologically-active agents.

To form the film dressing, the liquid composition is dispensed to a tissue site, whereupon the solvent diffuses or dissipates. The thermoplastic polymer is substantially insoluble in aqueous-based fluid and upon contact with an aqueous-based fluid it coagulates or solidifies to form a film or gelatinous matrix. The film can be nonporous or microporous. When the film is microporous, pores can be formed in the film either uniformly or asymmetrically as the solvent and optional pore forming agent diffuse or dissipate out of the coagulating or solidifying matrix. The liquid composition can be dispersed from a spray apparatus comprised of a vessel with a dispensing means, and preferably the dispensing means is an aerosol propellant with associated valve mechanism. When the film dressing is administered to an injured tissue site, it provides a cohesively strong, adhesive, biodegradable, mechanical and microbial barrier which is optionally capable of delivery of biologically-active therapeutic agents. When the film dressing is used as a topical transport reservoir for pharmaceutical agents, it binds intimately to the skin and is capable of delivering appropriate doses of the agent.

Thermoplastic Polymer Composition

Thermoplastic polymers useful in the film dressing and liquid composition of the invention include biologically and/or pharmaceutically compatible polymers that are bioerodible and biodegradable. Highly preferred thermoplastic polymers have a low Tg so that they are soft and flexible, yet also adhesive and cohesively strong. The thermoplastic polymer can also provide for water diffusivity, preferably within the range of about $2 \times 10^{-6}$ to $500 \times 10^{-6}$ gm/cm$^2$/hr, more preferably about $10 \times 10^{-6}$ to $200 \times 10^{-6}$ gm/cm$^2$/hr. The thermoplastic polymers are substantially insoluble in aqueous or body fluids, but are capable of dissolving or dispersing in a water miscible carrier or solvent to form a solution or dispersion. Upon dissipation of the solvent component and contact with an aqueous based fluid, the thermoplastic polymers are capable of coagulating or solidifying to form a solid or gelatinous matrix suitable for use as the film dressing.

The kinds of thermoplastic polymers suitable for the film dressing and liquid composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are highly preferred thermoplastic polymers. Optionally, the first two can be combined with glycolide to enhance the solubility of the polymer in the organic solvent of the composition.

The thermoplastic polymer is combined with a suitable organic solvent to form a dispersion or solution. The solubility or miscibility of a polymer in a particular solvent will vary according to factors such as crystallinity, hydrophilicity, capacity for hydrogen-bonding and molecular weight of the polymer. Consequently, the molecular weight and the concentration of the polymer in the solvent are adjusted to achieve desired miscibility. Highly preferred thermoplastic polymers are those which have solubility parameters which include a low degree of crystallization, a low degree of hydrogen-bonding, low solubility in water, and a high solubility in organic solvents. In addition, the molecular weight and concentration of the polymer in the solvent can be adjusted to achieve the desired viscosity. The liquid composition preferably has a viscosity which effectively provides for aerosolization of the composition while maintaining sufficient adhesion and cohesive strength of the film dressing. A viscosity that effectively provides for aerosolization is a viscosity which provides the liquid composition with flow properties and surface tension sufficient to allow for formation of small droplets in an aerosol. The viscosity can also be such that the evaporation of the solvent is not rapid enough to prevent coalescence of the aerosol drops on the surface of the tissue in the formation of the film dressing. Suitable solution viscosities include about 0.1 to 2000 cps, preferably about 1 to 100 cps, more preferably about 1 to 50 cps.

According to the invention, the liquid composition is administered to a tissue site, whereupon the solvent dissipates. Upon contact with the surrounding aqueous fluids, the polymer moiety coagulates or solidifies to form a solid or gelatinous matrix for use as a film at the tissue site. The solvent can evaporate or quickly diffuse into the surrounding tissue fluids or aqueous-based fluids to enhance formation of the polymer matrix following administration of the composition to the tissue site.

Preferably, the polymer matrix or film dressing is capable of adhering to the adjacent tissue by mechanical forces to at least partially bind or attach the film to the adjacent tissue, and/or mechanically bind two tissues together. The film dressing is preferably microporous but can also be substantially nonporous. When the film is microporous, it provides for diffusivity of water, oxygen, nutrients, and wound exudate to and/or from the tissue site. The film can also provide for very low oxygen and water diffusivity depending on the presence, size and distribution of pores. A substantially nonporous film allows for no diffusivity of water and oxygen. Both porous and substantially nonporous films can provide an adhesive, strong, flexible, biodegradable, mechanical, and microbial barrier.

Solvents

Solvents suitable for the liquid composition are those which are biocompatible, preferably pharmaceutically acceptable, and miscible with the polymer component and water. Preferably, the solvent has a Hildebrand (HLB) solubility ratio of from about $9(cal/cm^3)^{1/2}$ to $13(cal/cm^3)^{1/2}$. The degree of polarity of the solvent should be effective to provide at least about 10% solubility in water, and to dissolve, disperse or suspend the polymer component into solution. The solvent can be a liquid aerosol propellant or compatible with gaseous aerosol propellant so that the gaseous propellant can dissolve to some extent into the solvent. Upon application to a tissue site, the solvent diffuses into the adjacent tissues or into an aqueous medium. The concentration of polymer in the solvent for the liquid composition will generally accomplish rapid and effective dissipation of the solvent and coagulation of the polymer. This concentration can range from 0.01 g of polymer per ml of solvent to a 2 g per ml solvent, preferably from 0.08 g per ml to 1.2 g per ml solvent.

Solvents which can be used in the thermoplastic polymer composition of the invention include, for example, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, amides such as N,N-diethyl-m-toluamide, and 1-dodecylazacycloheptan-2-one. Preferred solvents according to the invention include N-methyl-2-pyrrolidone, 2-pyrrolidone, ethyl lactate, propylene carbonate, dimethyl sulfoxide and acetone.

Solvents which also can be used are those that are liquid aerosol propellants, for example, trichloromonofluoromethane, dichlorodifluoromethane, dichloromonofluoromethane, 2-tetrafluoroethane, 1,1-dichloro-1,2,2,2-tetrafluoroethane, 1-chloro-1,1-difluoroethane, 1,1-difluoroethane, octofluorobutane, propane, isobutane, N-butane, and mixtures thereof.

A mixture of solvents can be used to increase the coagulation rate of polymers which exhibit a slow coagulation or setting rate. For example, the polymer can be combined with a coagulant-promoting solvent system composed of a mixture of a good solvent and a poorer solvent or a non-solvent for the polymer component. It is preferred that the solvent mixture contain an effective amount of the two solvents such that the polymer will remain soluble in the mixture but coagulate upon dissipation or diffusion of the solvents into surrounding tissue fluids at the tissue site.

Pore Formation and Porosity

Upon contact with an aqueous body fluid or water, the liquid composition coagulates or solidifies to form a film. The film can be microporous or substantially nonporous. In a microporous film embodiment, pores can be formed in the film by dissipation, dispersement or diffusion of the solvent and an optional pore forming agent out of the solidifying polymer matrix. The size and distribution of pores can be asymmetric so that a two-layer core and skin structure is formed, or they can be uniform. Preferably the amount, size, and distribution of the pores provide for water diffusivity, cohesive strength, and a barrier to microorganisms.

Figure 2:
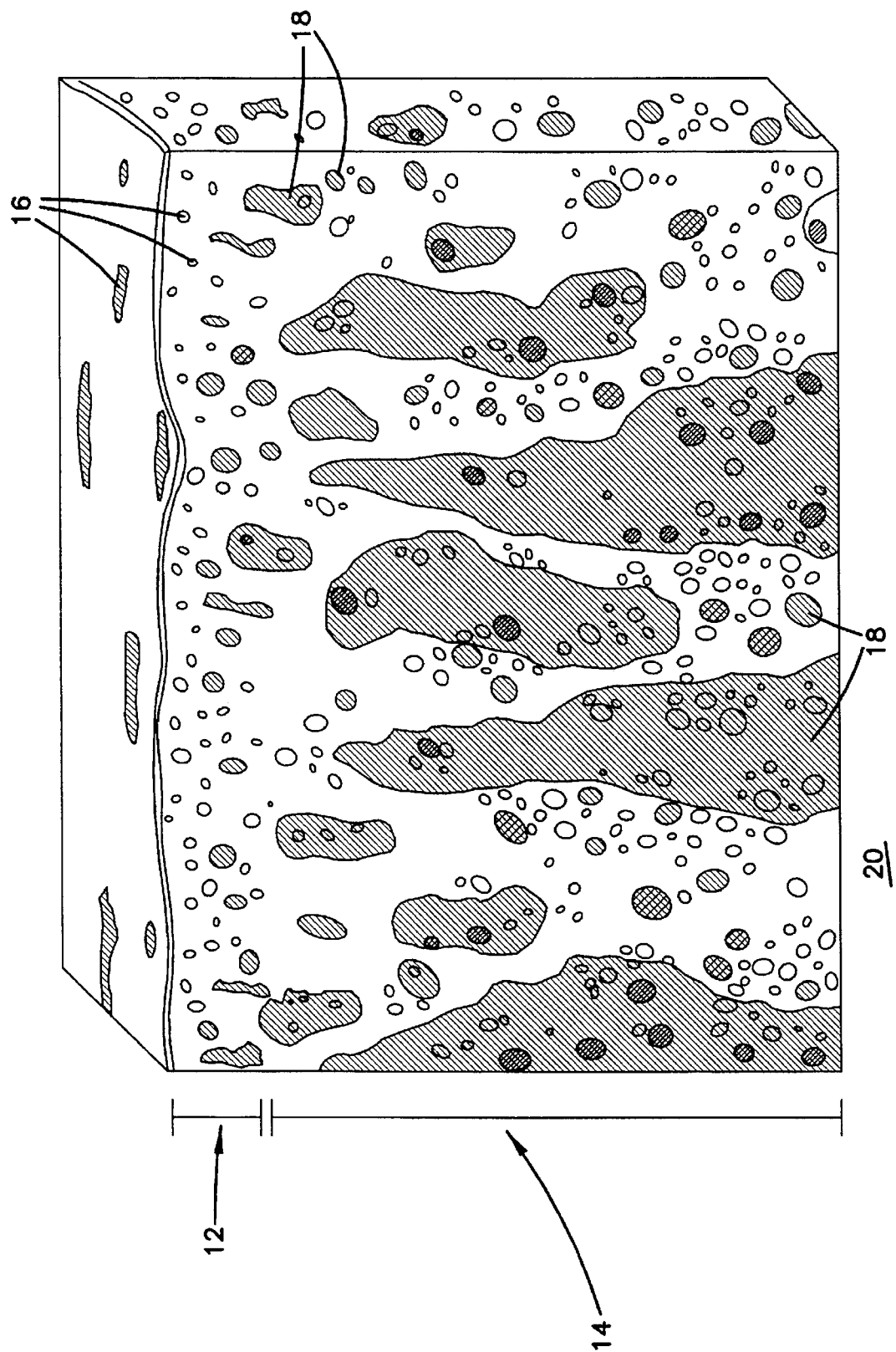
FIG. 2 is a depiction of a cross-sectional view of an embodiment of a microporous film dressing formed on skin tissue showing a two-layered pore structure with a skin portion and a core portion.

In a preferred version, the film dressing has a two-layered asymmetric pore structure composed of a core portion and a skin portion. The skin portion has pores with significantly smaller diameters than that of the pores in the core portion. The skin portion can be formed on top of the core portion with the core portion in contact with the tissue, or the skin portion or layer may be under the core portion and in contact with the tissue. FIG. 2 shows a cross-sectional view of a microporous film dressing (10) formed on skin tissue (20) showing a two-layered pore structure with a skin portion (12) formed on top of the core portion (14) in contact with the skin tissue (20). As shown, the pores (16) of the skin portion (12) are smaller diameter than the pores (18) of the core portion (14). Alternatively, the film dressing can have a homogeneous pore structure with pores evenly distributed throughout the film dressing.

A pore forming agent can be included in the liquid composition to generate additional pores in the polymer matrix. Pore forming agents include any pharmaceutically acceptable organic or inorganic water-soluble substance that is substantially miscible in water and body fluids and will dissipate from the in situ formed microporous film. In one version, the pore forming agent is biocompatible, and soluble in body fluids and water as well as in the organic solvents. The pore forming agent can also be insoluble in organic solvents and soluble in body fluids and water. The pore forming agent can also be soluble or insoluble in the organic solvent, and insoluble in body fluids and water, but can degrade to a water-soluble agent. The pore forming agent is capable of diffusing or dispersing out of the coagulating polymer matrix and into the adjacent fluid, whereupon pores are generated in the polymer matrix.

The pore forming agents, when combined with the thermoplastic polymer and solvent, preferably form a uniform mixture of a dispersion or suspension or a solution. When the mixture is administered to a tissue site, the solvent and/or pore forming agent preferably dissipate or diffuse, causing the formation of microporous channels within the coagulating polymer matrix. Optionally, the pore forming agent can become incorporated into the polymer matrix, and dissipate into the surrounding tissue fluids at a rate slower than that of the solvent, or be released from the matrix by the biodegradation or bioerosion of the implant matrix. As the slowly dissipating pore forming agent dissipates or diffuses into the surrounding tissues, it can also act to enhance percutaneous absorption of any biologically active agents.

Suitable pore forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The concentration of pore-forming agent relative to polymer in the composition will vary according to the degree of pore-formation desired. Generally, this concentration will range from 0.01 g of pore-forming agent per gram of polymer to about 1 g per gram of polymer.

The size or diameter of the pores formed in the matrix can be modified by the size and/or distribution of the pore-forming agent within the polymer matrix. For example, pore-forming agents which are relatively insoluble in the polymer matrix, can be selectively included in the composition according to particle size to generate pores having a diameter which corresponds to the size of the pore-forming agent. Pore-forming agents which are soluble in the polymer mixture can vary the pore size and porosity of the polymer mixture according to the pattern of distribution and/or aggregation within the mixture and resulting polymer matrix. Suitable size and distribution of pores are those allowing for water diffusivity while maintaining complete barrier properties to microorganisms and providing for cohesive strength of the microporous film.

To provide an effective microporous film, it is preferred that the diameter of the pores be about 3–500 microns, more preferably about 3–200 microns, and even more preferably about 3–100 microns, and most preferably 3–50 microns. It is further preferred that the matrix has a porosity of about 5–95%, preferably about 25–85% in order to provide preferred water diffusivity, preferred exchange of nutrients and oxygen, preferred structural integrity including cohesive strength, and an preferred barrier to microorganisms.

Biologically-Active Agents

The in situ formed microporous film can also provide a delivery system, including a transdermal delivery system, for biologically-active agents to adjacent or distant body tissues and organs. Biologically-active agents which can be used alone or in combination in the present compositions include medicaments, drugs, or any suitable biologically-, physiologically- or pharmacologically-active substance which is capable of providing local or systemic biological or physiological activity in a human or animal. The biologically-active agent must be capable of being released from the polymer matrix into the adjacent or surrounding aqueous fluid and/or tissues.

The biologically-active agent can be miscible in the polymer and/or solvent to provide a homogenous mixture with the polymer, or insoluble in the polymer and/or solvent to form a suspension or dispersion with the polymer. Upon administration of the composition to the tissue site, the biologically-active agent preferably remains or becomes incorporated into the polymer matrix. As the matrix biodegrades and/or bioerodes, the biologically-active agent can be released from the matrix into the adjacent tissue. Preferably, the biologically-active agent is released into the adjacent tissue at a controlled rate. For example, the polymer matrix can be formulated to degrade after an effective and/or substantial amount of the biologically-active agent is released from the matrix. Release of a biologically-active agent having a low solubility in water, as for example a peptide or protein, can require the degradation of a substantial part of the polymer matrix to expose the agent directly to the surrounding tissue fluids or can require the presence of a release modifying agent. Thus, the release of the biologically-active agent from the matrix can be varied by, for example, the solubility of the biologically-active agent in water, the distribution of the biologically-active agent within the matrix, or the size, shape, porosity, solubility and biodegradability of the polymer matrix, among other factors.

The composition and in situ formed film contain the biologically-active agent in an amount effective to provide the desired biological, physiological, pharmacological and/or therapeutic effect, optionally according to a desired release profile, and/or time duration of release. It is further preferred that the biologically-active agent is included in the polymer composition in an amount effective to provide an acceptable solution or dispersion viscosity. The film can function in wound healing or as a transdermal delivery system for the biologically active agent.

The biologically-active agent can also be a substance, or metabolic precursor thereof, which is capable of promoting growth and survival of cells and tissues, or augmenting the activity of functioning cells, as for example, blood cells, neurons, muscle, bone cells, epithelial cells and tissues, and the like. For example, the biologically-active agent can be a nerve growth promoting substance, as for example, a ganglioside, phosphatidylserine, a nerve growth factor, brain-derived neurotrophic factor, a fibroblast growth factor, fibronectin (FN), endothelial cell growth factor (ECGF), cementum attachment extracts (CAE), human growth hormone (HGH), a periodontal ligament cell growth factor, human or animal growth hormones, platelet derived growth factor (PDGF), epidermal growth factor (EGF), protein growth factor interleukin-1 (IL-1), transforming growth factor (TGFβ-2), insulin-like growth factor II (ILGF-II), human alpha thrombin (HAT), osteoinductive factor (OIF), bone morphogenetic protein (BMP), or proteins derived therefrom and releasing factors thereof.

Suitable biologically-active agents also include substances useful in preventing infection at the tissue site, as for example, antiviral, antibacterial, antiparasitic, and antifungal substances and combinations thereof.

The delivery system can contain a large number of biologically-active agents either singly or in combination. Examples of these biologically-active agents include, but are not limited to:

Anti-bacterial agents such as penicillins, cephalosporins, vancomycin, bacitracin, cephalosporins, polymxyins, amikacin, doxycycline, nystatin, amphotericin-B, tetracyclines, chloramphenicol, erythromycin, neomycin, streptomycin, kanamycin, gentamicin, tobramycin, clindamycin, rifampin, nalidixic acid, flucytosine, griseofulvin, and the like;

Antiviral agents such as vidarabine, acyclovir, ribavirin, amantadine hydrochloride, interferons, dideoxyuridine, and the like;

Antifungal agents such as nystatin, gentamicin, miconazole, tolnaftate, undecyclic acid and its salts, and the like;

Antiparasitic agents such as quinacrine, chloroquine, quinine, and the like;

Anti-inflammatory agents such as progesterone, hydrocortisone, prednisone, fludrocortisone, triamcinolone, dexamethasone, betamethasone, and the like;

Antihistamines such as diphenhydramine, chlorpheneramine, chlorcyclizine, promethazine, cimetidine, terfenadine, and the like;

Anaesthetics such as cocaine, benzocaine, novocaine, lidocaine, bupivocaine, and the like;

Analgesic agents such as salicylic acid, salicylate esters and salts, acetaminophen, ibuprofen, morphine, phenylbutazone, indomethacin, sulindac, tolmetin, zomepirac, and the like;

Antineoplastic agents such as methotrexate, 5-fluorouracil, bleomycin, tumor necrosis factors, tumor specific antibodies conjugated to toxins, and the like;

Growth factors such as colony stimulating factor, epidermal growth factor, erythropoietin, fibroblast growth factor, neural growth factor, human growth hormone, platelet derived growth factor, insulin-like growth factor, and the like;

Hormones of natural and synthetic origin as well as hormone regulatory agents such as insulin, FSN, ACTH, testosterone, anti-fertility compounds, estrogen, calcitonin and the like;

Kerolytic agents such as benzoyl peroxide, salicylic acid, trichloroacetic acid, piroctone, and wart treatment compounds such as salicylic acid, trichloroacetic acid and lactic acid, singularly or in combination with antiviral agents;

Tranquilizers of major and minor physiological activity as well as CNS pharmaceuticals;

Vitamins and vitamin derivatives such as Vitamin A, retinol, retinoic acid, α-tocopherol (Vitamin E), 7-dehydrochloresterol (Vitamin D), Vitamin K, thiamine riboflavin, niacin, pyridoxine, biotin, antothenic acid, ascorbic acid, choline, inositol, and the like.

The biologically-active agent can be included in the compositions in the form of, for example, an uncharged molecule, a molecular complex, a salt, an ether, an ester, an amide, or other form to provide the effective biological or physiological activity.

Choice of the particular biologically active agent or agents will depend upon the malcondition or condition to be treated, which choice will be made by the attending health care professional. Without a bioactive agent, the composition can function as a structure to promote cell growth and tissue repair and/or to bind or hold tissue together or to keep tissue apart. With a bioactive agent, the composition will not only function in such capacity but will also function to deliver the bioactive agent.

The amounts and concentrations of composition administered to the patient will generally be sufficient to accomplish the task intended. If that task is for administration of bioactive agent, the amounts and release rates will follow recommendations of the manufacturer of the bioactive agent. Generally, the concentration of bioactive agent in the liquid polymer matrix will be from 0.01 mg per g of matrix to 400 mg per g of matrix.

Other Additives

Depending on the desired properties of the film dressing, other additives can be incorporated into the liquid composition. Additives can effect both drug release and mechanical properties of the film. Such modifiers can be added in effective amounts to increase flexibility, to control permeability, to slow drug release, to increase percutaneous absorption of biologically active agents, and to monitor biodegradability. By way of example, the modifier triethyl citrate can be combined with the liquid composition to modify the function of the film by controlling permeability and to slow drug release.

Examples of suitable modifiers include phthalic esters, benzylphthalates, glycol benzoates, trimellitates, adipates, azelates, sebacates, esters of aliphatic and aromatic di- and tricarboxylic acids, organic phosphates, sesame, soybean and other oils.

Examples of suitable compounds which can be added to increase percutaneous absorption of biologically active agents include propylene glycol, glycerol, urea, diethyl sebecate, sodium lauryl sulfate, sodium laurye sulfate, sorbitan ethoxylates, oleic acid, pyrrolidone carboxylate esters, N-methyl pyrrolidone, N,N-diethyl-m-toluamide, dimethyl sulfoxide, alkyl methyl sulfoxides, and mixtures thereof.

Colorants can also be added to the liquid composition in an amount effective to allow monitoring of the biodegradability or bioerodibility of the microporous film over time. Colorants are nontoxic, non-irritating and non-reactive with the solvent in the liquid composition. Colorants which have been approved by the FDA for use in cosmetics, foods and drugs include: D & C Yellow No. 7; D & C Red No. 17; D & C Red No. 7, 9, and 34; FD & C Red No. 4; Orange D & C No. 4; FD & C Blue 2; FD & C Green No. 3, and the like.

Spray Apparatus for Delivery of the Liquid Composition

The liquid composition can be dispensed on a tissue site by painting, dropping, squirting and preferably by spraying. The spray apparatus of the present invention includes a liquid composition of the thermoplastic polymer in an organic solvent in a vessel with a dispensing means for spray delivery of the liquid composition to the human or animal tissue. In an alternative embodiment, the spray apparatus contains a liquid composition of thermoplastic polymer in a liquid aerosol propellant.

The vessel of the present invention is chosen from a variety of types of vessels depending on the method of dispensing the liquid composition. By way of example, when the dispensing means is an aerosol propellant with a valve and nozzle mechanism, the appropriate vessel is one which can withstand pressure generated by the presence of the aerosol propellant within the vessel. These pressure vessels are usually cylindrical in shape and composed of iron, aluminum alloys, glass or, plastic. Other suitable vessels include bottles, tubes, pads and the like.

The dispensing means can be any chemical, mechanical or electrical component which acts to propel the liquid composition as a liquid stream, liquid droplets or atomized spray from the vessel. The dispensing means can be a pump, a fluid pressurizing component, a collapsible vessel with a tube or jet, or an aerosol propellant with associated valve mechanisms. By way of example, another suitable spraying device would include a device for use in surgery having a vessel holding the liquid composition which is in fluid connection to a nozzle, the liquid composition being delivered to the nozzle by means of a pump, and the nozzle being actuated electronically so that delivery of the liquid composition can be controlled, as necessary, by the surgeon. The preferred dispensing means is a compatible aerosol propellant with valve mechanism which enables spray delivery of the liquid composition onto a human or animal tissue.

Aerosol Propellants

The dispensing means of the spray apparatus can be comprised of at least one aerosol propellant. The aerosol propellant can be a liquefied or compressed gas which acts to dispense the liquid composition from a pressurized vessel upon actuation of a valve in the dispensing means. The liquid composition can be delivered as a wet spray, fine spray, or a foam depending on the type of aerosol propellant employed. In the case of a liquid aerosol propellant, it is preferred that the propellant or propellants are substantially miscible with the organic solvent of liquid composition so that when the aerosol propellant is added to the liquid composition, a solution is formed. Alternatively, the liquid aerosol propellant can be similar in density to the liquid composition so that a uniform spray can be delivered upon mild shaking. In the case of a gaseous aerosol propellant, it is preferred that the gaseous propellant be somewhat soluble in the organic solvent of liquid composition.

In another embodiment, the thermoplastic polymer can be combined with a liquid aerosol propellant as solvent. In this case, the liquid aerosol propellant should be a solvent for the thermoplastic polymer and be present in an effective amount so that the thermoplastic polymer and propellant are delivered to the tissue site in a liquid form. Once the tissue site is contacted, the aerosol propellant rapidly dissipates and the thermoplastic polymer is coagulated or solidified upon contact with an aqueous based fluid to form a microporous film.

Suitable liquefied aerosol propellants include blends of fluorochlorohydrocarbons, chlorinated hydrocarbons, and hydrocarbons. Examples of fluorochlorohydrocarbons include trichloromonofluoromethane, dichlorodifluoromethane, dichloromonofluoromethane, 2-tetrafluoroethane, 1,1-dichloro-1,2,2-tetrafluoroethane, 1-chloro-1,1-difluoroethane, 1,1-difluoroethane, and octofluorocyclobutane, and mixtures thereof. Examples of hydrocarbons include liquefied petroleum gases like propane, isobutane, and N-butane and mixtures thereof. The compressed gas propellants are preferably non-toxic, non-flammable, and inert. Examples include carbon dioxide, nitrous oxide and $N_2$ and the like.

The aerosol propellant is present within the vessel so that it is either mixed with or, in the case of a gaseous propellant, in contact with the liquid composition. Alternatively, the liquid composition can be held within a chamber separated from the propellant by a barrier which responds to pressure exerted by the propellant to deliver the liquid composition. In another alternative embodiment, the spray apparatus can have a co-dispensing valve and system so that two ingredients can be kept separate until dispensed. The product components are dispensed in stoichiometric amounts and thoroughly mixed as they are delivered to the tissue site. For example, the liquid composition of thermoplastic polymer in an organic solvent can be held separate from a biologically active agent until they are co-dispensed and mixed upon delivery.

Method of Forming the Biodegradable Film Dressing

The invention also provides a method of forming a biodegradable film dressing on human or animal tissue. The film is formed on the tissue by dispensing an effective amount of the liquid composition of the thermoplastic polymer in the organic solvent and contacting the liquid with an aqueous based fluid to coagulate or solidify the film onto the human or animal tissue. An effective amount of the liquid composition is that amount which results in a film covering the tissue site, provides for a mechanical and microbial barrier and optionally provides a sufficient amount of a biologically active agent. Preferably an effective amount can be that amount which forms a film with a thickness within the range of about 0.001 to 5 mm, more preferably about 0.01 to 2.5 mm, and most preferably about preferably about 0.1 to 2 mm.

The liquid composition can be administered to skin, a surgical incision site, a body cavity, a burn, or to a site of tissue injury. The liquid can be delivered to form a patch, a bandage, a suture or to hold tissue apart as a surgical barrier. The liquid composition can be applied to exterior surfaces like skin or mucous membranes or to internal surfaces of organs, bones, and nerves that are accessible by surgery. When the film is functioning as a delivery system for biologically active agent, the film can be preferably formed as a patch or bandage or wound dressing. In a preferred version, the film dressing acts as a transdermal delivery system for biologically active agents and is applied to the skin or mucous membrane as a patch or bandage.

The liquid composition is dispensed by painting, dropping, brushing, squirting and preferably by spraying. The solvent rapidly diffuses or dissipates into the surrounding tissue and, upon contact with an aqueous based fluid, the thermoplastic polymer coagulates or solidifies to form a gelatinous matrix or a film dressing. A microporous embodiment can have a two-layered asymmetric pore structure with a core portion and a skin portion. The skin portion has pores with significantly smaller diameter than the pores of the core portion. Alternatively, the film dressing can have a homogeneous pore structure, or be substantially nonporous.

The aqueous-based fluid can be a body fluid already present at the tissue site, such as blood, serum, plasma, sweat, perspiration, and wound exudate and the like. The aqueous based fluid can alternatively be applied to the tissue site either before or after application of the liquid composition. A preferred aqueous based fluid is water, but suitable aqueous based fluids also include physiological solutions of sodium phosphate, sodium citrate, sodium acetate, sodium chloride, dextrose and sucrose, and the like. An aqueous based fluid can also be a formulation of a cream or an ointment containing at least one biologically active agent, preferably applied to the tissue site before the liquid composition is applied. The aqueous based fluid can be applied to the tissue site by painting, brushing, squirting, or preferably by spraying.

Method of Using the Film Dressing To Treat Injured Tissue

The liquid composition can be administered in an effective amount to an injured tissue site. The injured tissue site can be a surgical incision, a break in a bone, a skin or organ laceration, a burn, a rash, a vital lesion, a skin cancer or site of removal of a tumor, and the like. The damaged tissue can be external, such as skin, mucous membranes of the mouth, nose, vagina and rectum, and the eye. Alternatively, the damaged tissue can be an internal tissue or organ which is accessible during surgery. An effective amount of liquid composition is that amount which covers the injured tissue site with a film of sufficient thickness and porosity to provide for a mechanical and microbial barrier and a cohesively strong film with sufficient adhesion. The film can also provide for the exchange of oxygen, nutrients, water, and wound exudate to and from the tissue site. In addition, an effective amount can be that amount of the liquid composition which provides an effective amount of a biologically active agent.

The film can preferably be applied by spraying to the tissue site. The film can act to form a mechanical microbial barrier while allowing sufficient exchange of water, oxygen, nutrients and wound exudate. The film can also be sufficiently strong to bind or hold tissue together, like a suture or to hold tissue apart as a surgical barrier or to prevent internal and/or external adhesion between wounded, surgically abraded tissues so that fibrous bands otherwise causing adhesive of tissue are substantially reduced. Optionally, the film can act to deliver at least one biologically active agent which can promote wound healing and tissue regeneration, prevent infection and/or provide pain relief. By way of example, a film dressing containing an antibiotic and tissue growth factor may be sprayed onto burned skin where it could promote healing, prevent infection and regulate oxygen, water and nutrients to the tissue.

Administration of the composition as treatment for injured tissue ultimately will be accomplished according to the wisdom and protocol of the patent's attending health care professional. Choice of the particular composition, including which, if any, biological agents to add, will depend on the malcondition or condition to be treated, which choice will be made by the attending health care professional. Without a bioactive agent, the composition protects the injured tissue site from microbial and mechanical insults, binds tissue together, and promotes wound healing by ensuring adequate exchange of oxygen, nutrients, water and wound exudate. With a bioactive agent, the composition will function in such capacities and/or additionally provide the properties of the bioactive agent, like anti-inflammatory action or pain relief.

The invention will be described with reference to various specific and preferred embodiments and techniques, however, it should be understood that many variations and modifications can be made while remaining with the spirit and scope of the invention.

EXAMPLE 1

Film Biodegradability Study

A mixture comprising about 5% of an equimolar mixture of sodium carbonate and citric acid, about 60% N-methyl pyrrolidone, and about 3.5% of a 50/50 copolymer of poly(dl-lactide) and poly($\epsilon$-caprolactone) was prepared by suspending the sodium carbonate and citric acid in the polymer solution. The polymeric mixture was placed subcutaneously in rabbits to form a thick film in situ. The samples were left for 8 weeks. Polymers were recovered from subcutaneous sites and the recovered polymers were analyzed by gel permeation chromatography to determine molecular weight. No polymer could be found after two months indicating complete biodegradation.

EXAMPLE 2

Drug Release Profile

A mixture comprising about 5% of a 50/50 copolymer of poly(dl-lactide) and poly($\epsilon$-caprolactone), about 5% doxycycline, and about 85% N-methyl pyrrolidone was prepared according to Example 1. The polymer mixture was then sprayed onto a substrate and drug release was evaluated. The substrate was dialysis tubing incorporated into a diffusion cell and maintained at 37° C. One side of the diffusion cell was filled with phosphate buffered saline (pH=7.4) and the other with ambient air. The side of the dialysis tubing exposed to air was sprayed with the polymer mixture, and the diffusion of doxycycline out of the polymer film through the dialysis tubing and into the phosphate buffered saline was measured. Doxycycline in the phosphate buffered saline was detected by high performance liquid chromatography.

The results, summarized in FIG. 1, show that there was an initial burst of drug release in the first 4–6 hours. The initial burst was followed by slow release of the drug which was measured for at least 42 hours.

EXAMPLE 3

Drug Bioactivity Study

A mixture comprising about 5% of a 50/50 copolymer of poly(dl-lactide) and poly($\epsilon$-caprolactone), about 5% amikacin and 85% N-methyl pyrrolidone was prepared according to Example 1. A similar mixture was prepared but without amikacin as follows: about 5% of a 50/50 copolymer of poly(dl-lactide) and poly($\epsilon$-caprolactone) was mixed with 90% N-methyl pyrrolidone according to Example 1. Several agar plates seeded first with *Pseudomonas aeruginosa* were then sprayed with either a mixture containing polymer and amikacin, polymer alone or were untreated, and then observed for bacterial growth after 24 hours of incubation. No growth was seen on plates treated with the polymer/amikacin film, whereas untreated plates and plates with polymer film alone showed growth. The amikacin-containing polymer film was effective in preventing microbial growth indicating bioactive amikacin was released from the polymer film.

The polymer films were subsequently removed from the agar surface and the plates were re-inoculated with fresh viable *Pseudomonas aeruginosa*, and incubated for 24 hours. The results indicate that even after removal of the polymer containing amikacin no microbial growth was seen. The polymer control and untreated plates exhibited growth. The amikacin applied via the polymer film was released, diffused into the agar, and was bioactive in preventing the growth of *Pseudomonas aeruginosa* even after removal of the amikacin/polymer film.

EXAMPLE 4

Film Barrier Study

A mixture comprising about 5% of 50/50 copolymer of poly(dl-lactide) and poly($\epsilon$-caprolactone) and about 90% of N-methyl pyrrolidone was prepared according to Example 1. A similar mixture with amikacin was prepared as in Example 3. The mixtures were applied to sterile agar plates. The surface of the polymer film was inoculated with either a non-motile strain of *Staphylococcus aureus* or a motile strain of *Proteus vulgaris* and the plates were examined for growth after 24 hours of incubation. No growth was observed on plates with the polymer film indicating that the organisms could not diffuse or move through the polymer film to reach the agar surface. Growth was observed on plates inoculated in the absence of the polymer film.

The polymer film was then carefully removed and the plates reincubated for 24 hours. The results indicate that no growth was observed in the reincubated plates and, thus, the polymer film acted as an effective barrier to microbial growth by preventing organism penetration.

EXAMPLE 5

Water Diffusivity Study

A mixture comprising about 5% of 50/50 copolymer of poly(dl-lactide) and poly($\epsilon$-caprolactone) and 90% of N-methyl pyrrolidone was prepared according to Example 1. The mixture was sprayed onto one side of a very porous filter membrane. The membrane was placed in a chamber so that the polymeric film coated side was in contact with an aqueous solution at 37° C., and the other side of the membrane was in contact with dry nitrogen gas. The dry nitrogen gas was continually purged into a pre-weighed gas collection tube filled with desiccant. The increase in weight of the desiccant was used to calculate a water diffusivity value. The water diffusivity of the aerosoled polymer is about 60 gm/cm$^2$/hour$\times 10^{-6}$ intermediate between that of a very permeable barrier, like gauze (about 135 gm/cm$^2$/hr$\times 10^{-6}$), and a very nonpermeable barrier, like Saran® Wrap (about 2 gm/cm$^2$/hr$\times 10^{-6}$). The water diffusivity of the polymeric film is approximately equal to a wound dressing like Duoderm® (80 gm/cm$^2$/hr$\times 10^{-6}$).

EXAMPLE 6

Treatment for Burned Skin

A mixture can be prepared comprising about 5% of a 50/50 copolymer of poly(dl-lactide) and poly($\epsilon$-caprolactone), about 3% amikacin, 1% epidermal growth factor, 1% triethylcitrate, and 85% N-methyl pyrrolidone. The polymer mixture can then be loaded into a polyethylene vial equipped with a dip tube connected to a Freon™-loaded aerosol can. The polymer mixture will then be sprayed onto burned skin and evaluated for protection against infection and promotion of healing of the skin.

EXAMPLE 7

Wound Treatment

A mixture can be prepared comprising about 10% of a 50/50 copolymer of poly(dl-lactide) and poly($\epsilon$-caprolactone), about 0.5% polymyxin, about 0.5% vancomycin, and 89% N-methyl pyrrolidone. The polymer mixture will be loaded into a polyethylene vial equipped with a dip tube connected to a Freon™-loaded aerosol can. The polymer film will be sprayed onto a surgical incision to bind the incision together, like a suture. The polymer film will be evaluated for adhesion, flexibility, and wound healing.

EXAMPLE 8

Treatment of Rashes

A mixture can be prepared comprising about 8% of a 50/50 copolymer of poly(dl-lactide) and poly($\epsilon$-caprolactone), about 1% or less 1-(o-chloro-$\alpha$-$\alpha$diphenolbenzol)imidazole, 0.5% polymyxin b-sulphate, about 0.5% bacitracin, and 90% N-methyl pyrrolidone. The polymer mixture will be loaded into a polyethylene vial equipped with a dip tube connected to a Freon™-loaded aerosol can. The polymer film will then be sprayed onto a skin rash and skin will be observed for healing of the skin rash over time.

EXAMPLE 9

Treatment of Genital Herpes

A mixture can be prepared comprising about 1% of acyclovir, about 1% ibuprofen, about 10% triethylcitrate, and about 6% of a 50/50 copolymer of poly(dl-lactide) and poly($\epsilon$-caprolactone), and 83% N-methyl pyrrolidone. The polymer mixture will be loaded into a polyethylene vial equipped with a dip tube connected to a Freon™-loaded aerosol can. The polymer film will then be sprayed onto genital herpes lesions and will be evaluated for pain relief, healing, and capacity to act as a barrier to virus transmission.

EXAMPLE 10

Treatment of Mouth Sores

A mixture can be prepared comprising about 2% benzocaine, about 0.5% phenol, about 5.0% of a 50/50 copolymer of poly(dl-lactide) and poly($\epsilon$-caprolactone), and 97.5% N-methyl pyrrolidone. The polymer mixture will be loaded into a polyethylene vial equipped with a dip tube connected to a Freon™-loaded aerosol can. The polymer mixture will be sprayed onto mouth sores and evaluated for pain relief and wound healing.

What is claimed is:

1. A biodegradable microporous film dressing comprised of a skin and a core portion, the skin portion having pores with a smaller diameter than pores of the core portion; wherein the film dressing is formed by contacting a composition comprising a biodegradable thermoplastic polymer that is insoluble in aqueous or body fluids, and an organic solvent that is soluble in aqueous or body fluids, with an aqueous or body fluid whereupon the composition coagulates or solidifies to form the microporous film dressing.

2. The film dressing of claim 1, wherein the film dressing is formed by administering the composition onto a tissue, and the core portion of the film dressing is oriented under the skin portion and in contact with the tissue.

3. The film dressing of claim 1, wherein the film dressing is formed by administering the composition onto a tissue, and the skin portion of the film dressing is oriented under the core portion and in contact with the tissue.

4. The microporous film dressing of claim 1, wherein the biodegradable thermoplastic polymer is selected from the group consisting of polylactides, polyglycolides, polycaprolactones, polyethylene glycols, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(amino acids), poly(methyl vinyl ether) and copolymers, terpolymers, and combinations thereof.

5. The microporous film dressing of claim 1, wherein the organic solvent is selected from the group consisting of N-methyl-2-pyrrolidone, 2-pyrrolidone, acetone, acetic acid, ethyl acetate, ethyl lactate, methyl acetate, methyl ethyl ketone, dimethylformamide, dimethylsulfoxide, dimethyl sulfone, tetrahydrofuran, caprolactam, decylmethylsulfoxide, oleic acid, propylene carbonate, N,N-diethyl-m-toluamide, and 1-dodecylazacycloheptan-2-one, and mixtures thereof.

6. The microporous film dressing of claim 1, wherein the diameter of the pores of the skin portion and the core portion is about 3–500 microns.

7. The microporous film dressing of claim 1, wherein the biodegradable film is capable of providing a mechanical barrier, a microbial barrier, or a combination thereof, on a tissue.

8. The microporous film dressing of claim 1, wherein water, oxygen, nutrients, or a combination thereof, can diffuse through the film.

9. The microporous film dressing of claim 1, wherein the biodegradable film has a low oxygen permeability, low water permeability, or a combination thereof.

10. The microporous film dressing of claim 1, wherein the microporous film is capable of providing a transdermal delivery system of a biologically-active agent.

11. The microporous film dressing of claim 1, wherein the film dressing is administered to skin, a surgical incision, a body cavity, burn, tissue defect, or a combination thereof.

12. The microporous film dressing of claim 1, wherein the film dressing is in the form of a bandage, suture, surgical barrier, wound dressing, or combination thereof.

13. The microporous film dressing of claim 1, wherein the film dressing is formed by administering the composition onto a tissue, and the film dressing binds the tissue to another tissue.

14. The microporous film dressing of claim 1, wherein the composition has a viscosity that allows the composition to be aerosolized, and the composition is sprayed onto tissue and coagulates or solidifies to provide an adhesive and cohesive film dressing on the surface of the tissue.

15. The microporous film dressing of claim 1, further comprising a pore-forming agent.

16. The microporous film dressing of claim 15, wherein the pore-forming agent is a sugar, salt, or water-soluble polymer, or a water-insoluble polymer that degrades to a water-soluble polymer.

17. The microporous film dressing of claim 15, wherein the pore-forming agent is a polymer selected from the group consisting of hydroxylpropylcellulose, carboxymethylcellulose, polyethylene glycol, polyvinylpyrrolidone, and combinations and mixtures thereof.

18. The microporous film dressing of claim 1, wherein the composition further comprises a biologically-active agent.

19. The microporous film dressing of claim 18, wherein the biologically-active agent is selected from the group consisting of antibacterial agents, antiviral agents, antifungal agents, antiparasitic agents, anti-inflammatory agents, antihistamines, anaesthetics, analgesics, anticholinergic agents, anti-neoplastic agents, growth factors, hormones, hormone regulators, cardiovascular agents, tranquilizers, central nervous system agents, osteo-inductive agents, kerolytic agents, ultraviolet screening agents, antiperspirants, vitamins, and mixtures and combinations thereof.

20. The microporous film dressing of claim 18, wherein the biologically-active agent is capable of altering cell growth, bone growth, tissue regeneration, wound healing, nerve stimulation, or a combination thereof.

21. The microporous film dressing of claim 18, wherein the biodegradable film further comprises an agent capable of altering percutaneous absorption of the biologically active agent.

22. The microporous film dressing of claim 21, wherein the absorption altering agent is selected from the group consisting of propylene glycol, glycerol, urea, diethyl sebecate, sodium lauryl sulfate, sodium laurye sulfate, sorbitan ethoxylates, oleic acid, pyrrolidone carboxylate esters, N-methyl pyrrolidone, N,N-diethyl-m-toluamide, dimethyl sulfoxide, alkyl methyl sulfoxides, and mixtures thereof.

* * * * *